United States Patent [19]

Blake et al.

[11] 4,429,693

[45] Feb. 7, 1984

[54] SURGICAL FLUID EVACUATOR

[76] Inventors: Larry W. Blake, 2885 Regis La., Costa Mesa, Calif. 92621; Ervin R. Harvel, 23991 Lindley, Mission Viejo, Calif. 92675; Duane R. Mason, 31 Farragut, Irvine, Calif. 92664; George M. Wright, 24145 Puerta Deluz, Mission Viejo, Calif. 92675

[21] Appl. No.: 187,711

[22] Filed: Sep. 16, 1980

[51] Int. Cl.³ .............................................. A61M 1/00
[52] U.S. Cl. ..................................... 604/73; 128/765; 604/113; 604/119; 604/280
[58] Field of Search ............... 128/276, 277, 278, 302, 128/760, 767, 768, 297, 765; 417/472, 480, 92, 94; 267/62

[56] References Cited

U.S. PATENT DOCUMENTS

| | | | |
|---|---|---|---|
| 2,947,470 | 8/1960 | Rubin et al. | 128/278 |
| 2,965,907 | 12/1960 | Ropelato | 4/259 |
| 3,084,691 | 4/1963 | Shaft | 128/278 |
| 3,115,138 | 12/1963 | McElvenny et al. | 128/278 |
| 3,572,340 | 3/1971 | Lloyd et al. | 128/278 |
| 3,809,087 | 5/1974 | Lewis, Jr. | 128/278 |
| 3,889,677 | 6/1975 | Nehring | 128/278 |
| 4,111,407 | 9/1978 | Stager | 267/62 |
| 4,161,179 | 7/1979 | Abramson | 128/278 |
| 4,278,089 | 7/1981 | Hock et al. | 128/760 |

OTHER PUBLICATIONS

Cox-Uphiff International, DS-1, DS-2, and DS-3 Drainage Systems, 1977 copyright, (3 pages).
BIOMET CWS, Closed Wound Suction Systems, brochure-6 pages.
Heyer Schulte, U.S. Distributor: V. Mueller, brochure Suction Drain System, Apr. 78.
Davol, "To Generate More Suction More Easily, We Turned To Physics, and the Balloon," (4 pages).
Davol, ReliaVac Silicone Drains, Less Worry for the Doctor . . . Less Work for the Nurse . . . Less Trauma for the Patient, (4 pages).
Zimmer USA, A New Generation of Reliability and Convenience, Snyder Hemovac for Closed Wound Suction, etc., (5 pages).

*Primary Examiner*—Richard J. Apley
*Assistant Examiner*—J. L. Kruter
*Attorney, Agent, or Firm*—Knobbe, Martens, Olson, Hubbard & Bear

[57] ABSTRACT

A flexible, compressible reservoir draws a substantially constant vacuum to permit uniform removal of fluid from a surgical incision through a wound drain catheter. The reservoir includes a compression spring interposed between a pair of congruent articulated plates. The spring provides biasing force to expand the reservoir and create a vacuum therein. Each of the articulated plates has a central member hinged on opposite sides to wing members. As the reservoir expands, the wing members pivot relative to the central members to decrease the effective area to which the spring force is applied. Such decrease in the effective area permits the spring force per unit of area to remain more nearly constant, and thus, reduces changes in reservoir vacuum.

28 Claims, 17 Drawing Figures

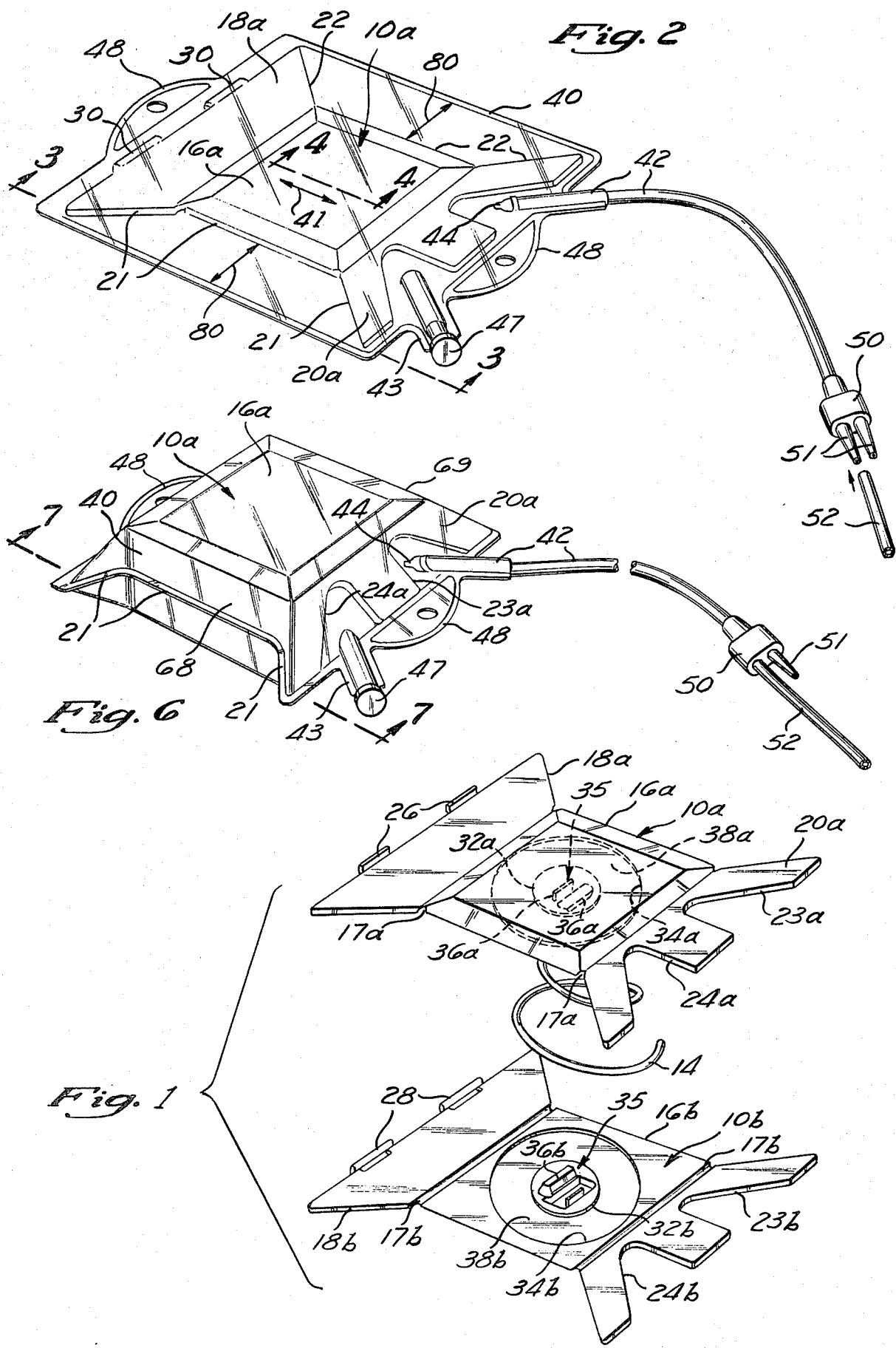

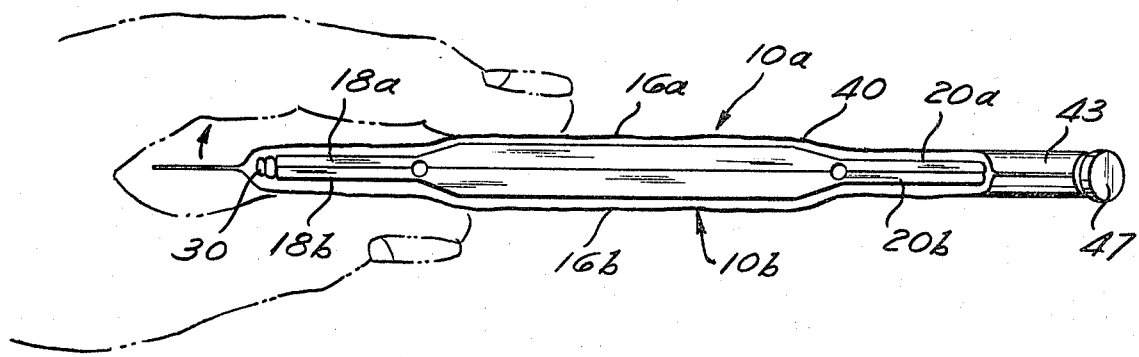
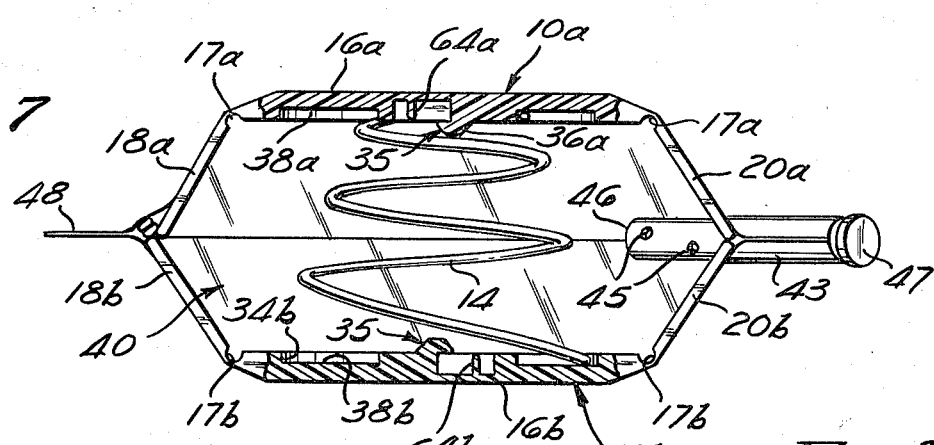
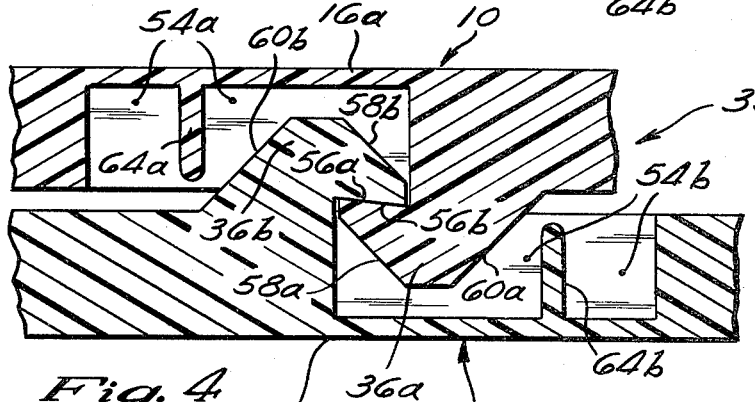
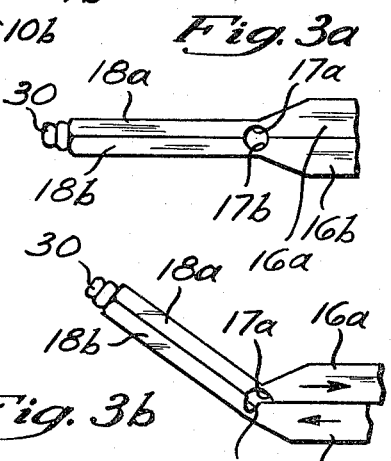
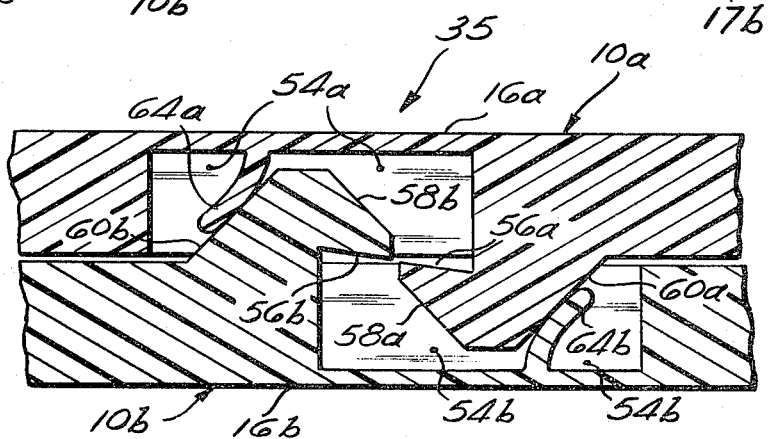

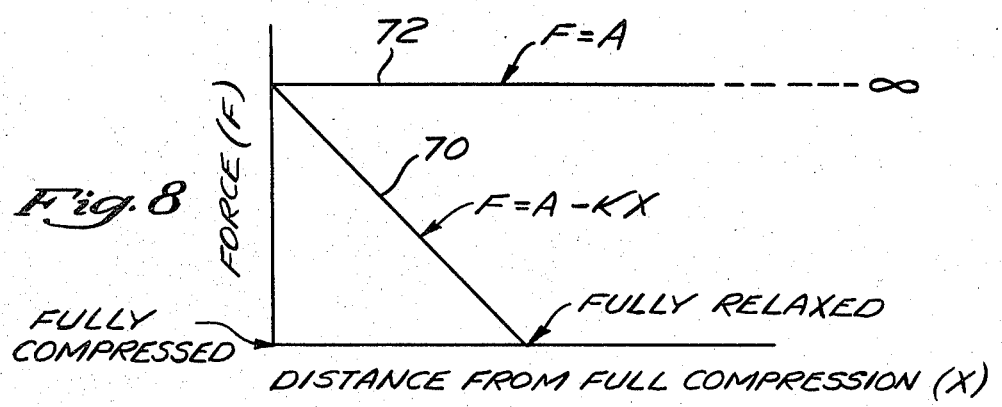
Fig. 8
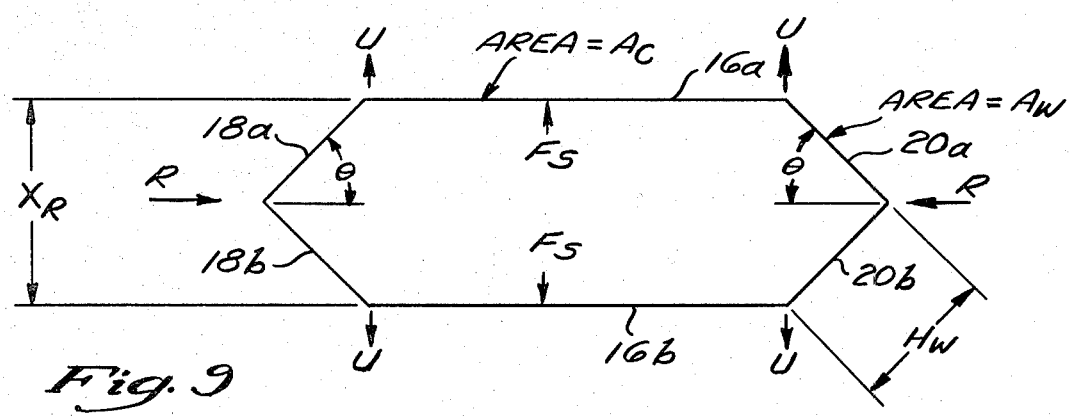
Fig. 9
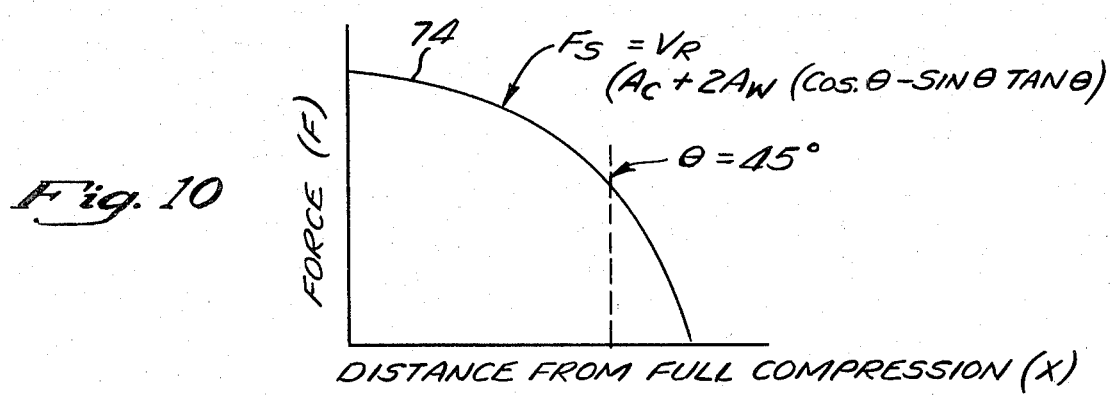
Fig. 10
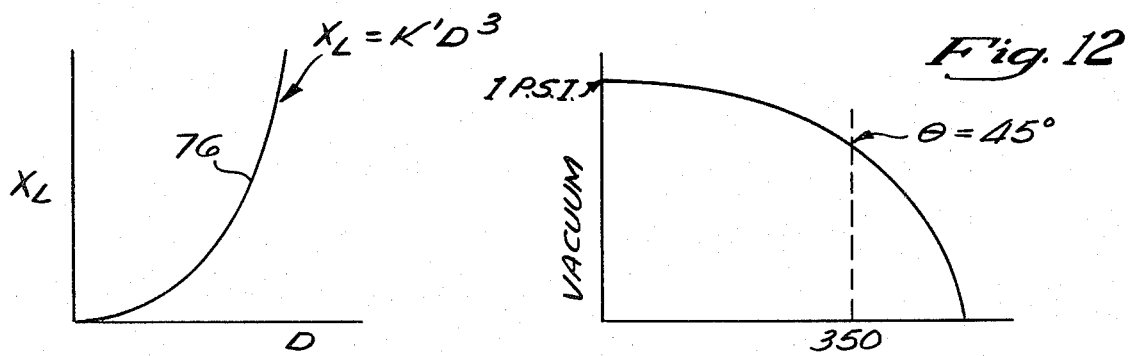
Fig. 11
Fig. 12

SURGICAL FLUID EVACUATOR

BACKGROUND OF THE INVENTION

This invention relates to portable fluid evacuators which are disposable and self-contained.

The practice of drawing a vacuum on a catheter placed in a patient's body to remove fluid buildup following surgery is a common medical technique. It has been found that removal of fluids from a wound will accelerate healing and reduce the risk of infection. Fluid evacuation has been typically accomplished by means of a central suction system or by power driven vacuum pumps. This has proven unsatisfactory because it is difficult or impossible to move the patient without first disconnecting him from vacuum supply. Further, the negative pressure supplied by such vacuum units is difficult to maintain at a constant value. Moreover, the use of power driven electric pumps is potentially hazardous since the fluid pathway through the wound drain catheter creates an electrical connection between the pump and the patient which exposes the patient to risk of shock or electrocution.

The prior art attempted to overcome these problems by providing portable, self-contained, non-electrical fluid evacuators. These evacuators typically comprise collapsible reservoirs biased with springs or weights which bias them to open after being manually compressed. Since these devices are self-contained and portable, the patient may be easily moved without disconnecting him from the device. However, many of these prior art devices are not capable of maintaining a substantially constant vacuum over their entire filling range. Constant vacuum pressure is desirable, since this permits uniform removal of fluid from the patient. If the vacuum is too high, lesions may be caused by sucking delicate tissue into or against the drainage tube. Conversely, if the vacuum is too low, fluid will accumulate and the device will be ineffective. Thus, a substantially constant pressure fluid evacuator is considered highly advantageous.

A further problem with prior art evacuators is that many of them are not pre-evacuated by the manufacturers, but rather, must be manually evacuated just prior to use. Typically, a nurse or medical assistant will apply force with one hand to manually compress and collapse the reservoir, and, with the other hand, insert a catheter or plug into the device before removing such compression force. Evacuation at the point of use is, therefore, awkward and time consuming.

An additional disadvantage of fluid evacuation devices which are evacuated at their point of use is that they are shipped in an unevacuated state. Thus, they require more storage space than the pre-evacuated devices. Obviously, this increases shipping, storage, and sterilization costs. Further, it is difficult, if not impossible, to completely evacuate a fluid reservoir at its point of use. Thus, when the reservoir is initially connected to draw fluid from the patient, it may still contain a substantial quantity of air. Since the space devoted to containing such air is wasted, the effective capacity of the reservoir is decreased. Therefore, the reservoir size must be larger than would otherwise be necessary. This increases manufacturing costs and further increases the costs of sterilization, shipment, and storage.

One reference, Abramson U.S. Pat. No. 4,161,179, suggests pre-evacuating a fluid evacuation device. The Abramson device comprises a flexible reservoir biased with leaf springs. Abramson teaches that after the reservoir has been pre-evacuated, the catheter is clamped to maintain the vacuum created by such pre-evacuation. Subsequently, after the catheter has been placed in the wound, the clamp is removed to permit the device to draw fluid. However, this method of maintaining a vacuum is obviously disadvantageous, since the clamp may be accidentally dislodged either during shipment or be a nurse while handling the device. Moreover, such a clamp, in order to maintain the vacuum, would have to exert considerable force on the catheter tube. Thus, if the device were stored for a long period of time, the resiliency of the catheter tube may not be sufficient to permit it to return to its normal shape, and the tube may remain permanently crimped. Therefore, the flow of fluid from the wound to the evacuator would be substantially restricted.

SUMMARY OF THE INVENTION

The present invention alleviates these and other problems of the prior art by providing a pre-evacuated flexible reservoir which houses an articulated, spring biased, skeletal mechanism. The skeletal mechanism and the reservoir cooperate to permit the reservoir to draw a vacuum at a substantially constant negative pressure. An internal latch is included within the skeletal mechanism to maintain the reservoir in a compressed, evacuated condition prior to use.

The skeletal mechanism comprises an essentially conical helical spring, interposed between two articulated plates. The spring biases the plates in opposite directions. Each of the plates includes a square or rectangular central member that is connected on opposite sides to respective wing members by integral hinges. Each of the two wing members is shaped as an isosceles trapezoid, and one of the two wing members has a pair of triangular notches. The central member and two wing members of each plate are of the same dimensions to permit the plates to be congruent. The plates are retained in a congruent position by means of hines on the ends of the unnotched wing members of the respective plates. Since the hinges are at the end of the unnotched wing members, they do not prevent the central members and two wing members from pivoting relative to each other as the reservoir fills.

The central members each have a spring cup to permit the spring to be retained therebetween. When the plates are pressed against one another, the individual coils of the conical biasing spring compress to nest within one another and within the recesses of the spring cups. Thus, when the spring is fully compressed, the two plates lie flat against each other with virtually no space therebetween. A latch is included within each of the respective spring cups to retain the spring, the skeletal mechanism, and the reservoir in a compressed state.

The plates, with the spring compressed therebetween, are sealed in the reservoir which comprises a rectangular plastic bag. The bag is limp or flexible, is sized to fit the overall length and width of the plates, and is stretched to insure that the plates fit snugly therein. Since the latch holds the spring in a compressed state, the plates lie flat against one another, thereby permitting the device to be manufactured and shipped in a thin, compact, and pre-compressed state. This significantly reduces the cost of sterilization, shipment, and storage. Further, such pre-compression eliminates the task of evacuating the device at its point of use by manually compressing it.

Although not essential, it is preferable to draw a vacuum on the reservoir after it is compressed and latched, but prior to shipment to the consumer. This is a convenient method of removing residual pockets of air from the reservoir. Further, such vacuum permits atmospheric pressure to exert force against the exterior surfaces of the two plates. This assists the latch in maintaining the device in a compressed state, and thereby reduces stress forces on the latch. Thus, the device may be stored in its pre-evacuated state for long periods of time without deformation of the latch mechanism. In addition, the vacuum effectively immobilizes the latch and thereby reduces the risk of accidental or inadvertent disengagement.

The reservoir includes a drain tube and a fluid collection tube which pass through the reservoir wall into the triangular notches, respectively, of the notched wing members. At the points where these tubes pass through the reservoir, they are sealed to the reservoir. These tubes extend well into the reservoir to reduce the likelihood that the reservoir wall might interfere with the flow of fluid. The fluid collection tube includes a check valve to prevent reverse flow of fluid from the reservoir to the patient. The drain tube includes perforations along its extension into the reservoir to assure that the reservoir will be completely drained even if the end of the drain tube is blocked. A plug or stopper is provided to seal the drain tube when not in use.

The end of the fluid collection tube outside the reservoir is terminated in a Y-fitting to permit the fluid evacuation device to be connected to one or two catheters. The Y-fitting is normally sealed to maintain the previously discussed vacuum in the reservoir. However, just prior to insertion into the catheter, a nurse or medical assistant will remove this seal. Thus, a small amount of air is permitted to enter the reservoir through the unsealed Y-fitting. Such air will not destroy the sterility of the device, since the Y-fitting seal is typically broken in an operating room environment. Further, the amount of air entering the reservoir is so small that it will have little, if any, effect on the fluid capacity of the device. However, the amount of air is sufficient to break the vacuum, and thereby permit the latch to function.

After the fluid collection tube is connected to the catheter, the surgical evacuator is activated simply by bending the unnotched wing members relative to the central members. Such bending causes the central plates to slide relative to one another, and thereby disengages the latch. This releases the conical spring, and thus, the spring will force the plates apart. As the distance between the plates increases, the volume of the reservoir will concommitantly increase. However, since the reservoir is sealed from the atmosphere, the volume of the reservoir cannot increase unless it draws fluid from the catheter. Thus, as the plates are forced apart, a suction or vacuum will be created to draw fluid into the reservoir.

The nominal value of reservoir vacuum for fluid evacuation purposes is typically 1 psi. It was a primary design consideration in the present invention to limit deviations in vacuum to less than 20% from the nominal value in the belief that such limitation will virtually eliminate the risk that the vacuum will cause lesions by sucking tissue into the catheter's drain tube. Further, it is believed that such limitation in vacuum pressure will insure that the device will have sufficient suction to prevent excessive fluid buildup. Accordingly, the present invention is designed to limit deviations in vacuum to ±20% throughout its operating range. This is accomplished both by the design of the spring and the unique geometry of the plates. As discussed above, the spring is conical to permit it, when compressed, to nest in the spring cups. Thus, the diameter of the spring coils will vary from one end to the other. It is well known that for a given type of spring material, the spring constant (i.e., the slope of the force versus distance curve) varies inversely according to the coil diameter. Thus, a conical spring typically has a non-linear spring constant. However, it is also well known that the spring constant varies directly with the pitch of the spring coils. Thus, the inherent non-linearity of the spring constant of a conical spring may be compensated for by varying the pitch of the spring coils. Accordingly, by increasing the pitch of the coils as the coil diameter increases, the spring of the present invention is formed to have an essentially linear spring constant.

The force exerted by the coils of a conical spring having a linear spring constant is directly proportional to the amount that they are compressed. Thus, as the conical spring forces the plates apart, the force exerted by such spring will progressively, linearly decrease as the distance between the plates increases. Such decrease in the force exerted by the spring is compensated for by the unique geometry of the plates. Specifically, it will be recalled that the plates are articulated by hinging each pair of wing members to its respective central member. Thus, as the central members are forced apart, their respective pair of wing members will pivot inward. Such inward movement of the wing members permits the spring to exert force over a progressively smaller effective plate area. Since both the spring force and this effective plate area decrease as the plates separate, the force per unit of area remains more nearly constant. Thus, such articulation of the plates compensates for the progressive decrease in spring force.

In addition, it will also be recalled that the reservoir is sized to fit snugly around the plates. Thus, the vacuum created by the expanding volume of the reservoir will force the reservoir wall inward against the articulated plates. Assuming that the central members lie in the horizontal plane, the horizontal component of the force exerted by the reservoir wall on the wing members will increase and the vertical component will decrease, as the wing members pivot inward at progressively increasing angles with respect to the central members. This horizontal force on the wing members will drive the wing members inward. Since the wing members are integrally hinged to the central members, the wing members will wedge against the central members to force them apart. Thus, such wedging force by the wing members against the central members further compensates for the loss of spring force as the central members spread apart. Therefore, the unique geometry of the present invention permits the spring force per unit of effective area to remain substantially constant, and thereby limits vacuum pressure deviations to ±20% to permit maintenance of a substantially constant negative pressure throughout the entire filling range of the device.

DESCRIPTION OF THE DRAWINGS

These and other advantages of the present invention are best understood through reference to the drawings, in which:

FIG. 1 is an exploded perspective view of the articulated plates with the spring interposed therebetween;

FIG. 2 is a perspective view of the plates, with the spring compressed therebetween, sealed in a flexible reservoir having a fluid collection tube and drain tube;

FIG. 3 is a cross-sectional view of the present invention in its compressed state, taken along the lines 3—3 of FIG. 2;

FIG. 3A is a partial, enlarged view of one wing portion of FIG. 3, showing the hinged connection between the central members and one pair of wing members in greater detail;

FIG. 3B is the same partial enlarged view of FIG. 3A showing the hinged connection interacting with the central members to slide the central members in opposite directions in response to bending the pair of wing members relative to the central members;

FIG. 4 is an enlarged, partial cross-sectional view of the plates 10, taken along the lines 4—4 of FIG. 2, showing the latch hooks engaging each other;

FIG. 5 is the same enlarged partial cross-sectional view of FIG. 4 showing the latch hooks disengaged as the plate 10 slides relative to each other according to FIG. 3B;

FIG. 6 is a perspective view of the present invention after the reservoir has expanded to its maximum volume;

FIG. 7 is a cross-sectional view taken along the lines 7—7 of FIG. 6, with part of the plates cut away to illustrate the position of the latch hooks on their respective plates;

FIG. 8 is a graph of spring force versus distance from full compression for a typical helical spring and for an ideal spring;

FIG. 9 is a schematic cross-sectional view of the present invention illustrating the forces acting on the articulated plates and defining some of the geometric relationships and characteristics of the plates;

FIG. 10 is a graph of spring force versus distance from full compression which approximates the spring characteristics necessary to achieve a constant reservoir vacuum for a given plate geometry;

FIG. 11 is a graph of spring coil pitch versus spring coil diameter for a single coil spring of a given material and for a given spring force at maximum compression;

FIG. 12 is a graph showing reservoir vacuum versus volume of fluid drawn into the reservoir for a given plate geometry and a spring having given characteristics;

DETAILED DESCRIPTION OF THE PREFERRED EMBODIMENT

Figure 14:
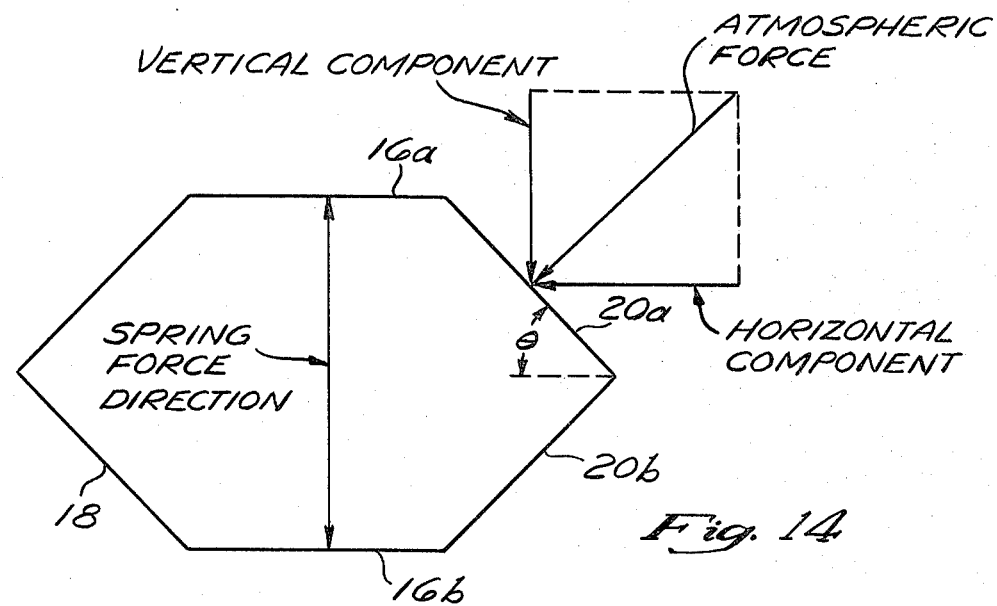
FIG. 14 is a schematic drawing of the reservoir of FIG. 13, but with the reservoir more fully expanded, showing that the vertical atmospheric force component decreases, and the horizontal atmospheric force component increases, as the reservoir expands.

Referring to FIG. 1, the present invention comprises a pair of congruent, articulated plates 10a and 10b with a conical helical spring 14 interposed therebetween. Each of the plates 10a,10b includes a respective square or rectangular central member 16a,16b which is connected by integrally formed hinges 17a,17b to respective trapezoidal wing members 18a,18b and 20a,20b. The trapezoidal wing members 18,20 are disposed on opposite sides of the central members 16 and have an isosceles configuration, with the shorter of their trapezoidal bases being hinged to the central member 16. Thus, the plates 10 are shaped essentially as rectangles with trapezoidal cut-outs 21,22 on opposite sides. The wing members 20a and 20b include a pair of essentially triangular notches 23a,24a and 23b,24b, respectively, while the wing members 18a and 18b are not notched. However, the wing member 18a includes a pair of upstanding hinge hooks 26 which are sized to be received by a pair of slots 28 in the wing member 18b.

The plates 10a and 10b include respective inverted spring cups or bosses 32a and 32b and respective recessed spring cups 34a and 34b. The spring boss 32 is sized to retain the small coil diameter end of the conical spring 14 while the spring cup 34 is sized to retain the large coil diameter end of the conical spring 14. Each of the plates 10 has both an inner spring boss 32 and an outer spring cup 34. Thus, either of the plates 10 may receive either end of the spring 14.

To assemble the evacuator, the plates 10a,10b are first hinged together, by inverting the plate 10a, inserting the hinge hooks 26 into the slots 28, and then rotating the plate 10a about the hooks 26. This assembly operation results in a congruent positioning of the plates 10, with a hinged connection therebetween at 30 (FIG. 2). The spring 14 is next compressed between the spring cups 32,34 of the plates 10.

The spring cups and bosses 32a,34a and 32b,34b form recesses 38a and 38b, respectively, in the plates 10a and 10b, respectively, to permit the fully compressed spring 14 to nest therein, and thereby permit the plates 10 to lie flat against each other with virtually no space therebetween (FIG. 3). A latch member or hook 36b, which protrudes from the interior face of the plate 10b, is provided within the spring boss 32b. The plate 10a has a similarly disposed latch member or hook 36a oriented 180 degrees with respect to the latch hook 36b. These latch hooks 36 form a latch 35 which retains the spring 14 in a compressed condition.

Referring to FIG. 2, the plates 10 with the compressed spring 14 retained therebetween are sealed in a rectangular reservoir or plastic bag 40. The reservoir 40 is sized to fit the overall dimensions of the compressed plates 10. Further, the reservoir 40 is stretched in a direction shown by the arrow 41 to ensure that the bag fits snugly around the plates 10. Since the plates 10 are not rectangular because of the trapezoidal cut-outs 21,22, the plates 10, therefore, will not contact the entire surface of the rectangular reservoir 40. As will be understood more fully below, the trapezoidal cut-outs of the plates 10 are included to permit the reservoir 40 to expand in volume as the device draws fluid from the patient.

A fluid collection tube 42 and drain tube 43 are connected to the reservoir 40. Both of the tubes 42,43 are sealed to the reservoir 40 at the point where they pass through the reservoir wall into the triangular notches 23,24, respectively, of the wing members 20. These tubes 42,43 extend well into the reservoir to reduce the likelihood that the reservoir wall will interfere with the flow of fluid. A check valve 44 is included on the end of the fluid collection tube 42 within the reservoir 40 to prevent reverse flow of fluid from the reservoir 40 to the patient. The drain tube 43 includes perforations 45 (FIG. 7) along its extension into the reservoir 40 to permit the reservoir 40 to be completely drained even if the end of the tube 43 is blocked. A plug or stopper 47 seals the drain tube when not in use.

The reservoir 40 also includes a pair of flanges 48 to permit the reservoir to be attached to the patient by a strap (not shown). The end of the fluid collection tube 42 is terminated in a Y-fitting 50 having two catheter connections 51 to permit it to be connected to one or two wound drain catheters 52. The Y-fitting 50 is normally sealed to prevent ambient air from entering the reservoir 40. However, just prior to connecting the catheter 52, a nurse or medical assistant will remove this seal, typically by cutting the end of the catheter connector 51.

The device may be precompressed by the manufacturer prior to shipment. As previously mentioned, the latch 35 retains the device in a precompressed state. However, it is preferable to also draw a vacuum on the reservoir 40 prior to shipment to completely evacuate any residual air contained in the reservoir 40. This vacuum permits atmospheric pressure to exert force on the walls of the reservoir 40 and thereby assists the latch 35 in maintaining the plates 10 in a precompressed state. Thus, stress forces on the latch hooks 36 are reduced and therefore the device may be stored in its pre-evacuated, precompressed state for substantial periods of time without deformation of the latch 35. Such precompression by the manufacturer also permits the device to be very compact, since the thickness of the device, when compressed, is equal to the combined thickness of the plates 10, or about ⅜ inch.

As will be understood more fully below, the vacuum prevents relative movement of the latch hooks 36 and thereby reduces the risk of accidental or inadvertent disengagement of the latch 35. Thus, when the evacuator is to be used, in order to disengage the latch 35, the vacuum must be broken. This is typically accomplished by breaking the previously described seal on the catheter connector 51 of the Y-fitting 50, thereby permitting a small amount of air to enter the reservoir 40. Since the seal is typically broken in an operating room environment, the sterility of the device will not be affected. Further, the quantity of air entering the reservoir is so small that its effect on the fluid capacity of the reservoir is insignificant. However, the quantity of air is sufficient to break the vacuum and thus permit the latch 35 to function.

Referring now to FIGS. 4 and 5, the details of the latch 35 will be described. As previously mentioned, the latch 35 is comprised of latch hooks 36a and 36b, which extend from the interior of the plates 10a and 10b, respectively. The plates 10a and 10b have respective cavities 54a and 54b which receive the latch hooks 36b and 36a, respectively. The latch hooks 36a and 36b have respective hooking surfaces 56a and 56b which engage each other to hold the plates 10 against one another, as shown in FIG. 4. These hooking surfaces 56 are inclined slightly relative to their respective plates 10 to inhibit them from sliding relative to each other, and thereby disengaging.

Referring to FIG. 3, the latches 35 may be disengaged by grasping the plates 10 between the fingers and thumb (shown in phantom) and bending the wing plates 18 upward with respect to the central plate 16. Such disengagement of the latch 35 is accomplished by forming the hinges 17 as semicircular slots which are disposed to face each other to form a cylindrical opening, as shown in FIG. 3A. Referring to FIG. 3B, as the wing members 18 pivot upward relative to their respective central members 16, the width of the slot forming the hinge 17a will decrease and the width of the slot forming the hinge 17a will concomitantly increase. Since the ends of the wing members 18 are connected together by the hinge 30, they will necessarily remain in a congruent position. Thus, the decreasing width of the slot of the hinge 17b will tend to slide the central member 16b towards the wing members 18 and the increasing width of the slot of the hinge 17a will tend to slide the central member 16a away from the wing members 18. Therefore, the central members 16 will slide relative to each other. Since the latch hooks 36a and 36b are attached to the central members 16a and 16b, respectively, they will also slide relative to each other. Such sliding is sufficient to change the position of the latch hooks 36 from that shown in FIG. 4 to that shown in FIG. 5, and thus permit the hooking surfaces 56 to disengage. Therefore, the latch 35 may be disengaged simply by bending the wing members 18 relative to the central members 16. Such disengagement permits the conical spring to separate the plates 10 and thereby enables the device to draw fluid into the reservoir 40.

Although it is preferable to dispose of the device after its first use, the device may, if desired, be drained, compressed, and reused. This is accomplished by removing the drain plug 46, emptying the reservoir 40 by manually pushing the plates 10 against one another to compress the spring 14, and reinserting the drain plug 46. The latch 35 is adapted to re-engage when the spring 14 is fully compressed. This is accomplished by providing respective closing cam surfaces 58a, 58b and biasing cam surfaces 60a, 60b on the latch hooks 36a, 36b. The closing cam surfaces 58 are inclined relative to their respective central members 16, and cooperate to force the biasing cam surfaces 60a, 60b against respective resilient biasing tabs 64b and 64a. These tabs 64a and 64b protrude from the respective cavities 54a and 54b of the respective plates 10a and 10b. As the latch hooks 36a and 36b descend into the cavities 54b and 54a, respectively, their biasing cam surfaces 60a, 60b will bend the tabs 64b and 64a, respectively, in opposite directions, as shown in FIG. 5. When the latch hooks 36 descend sufficiently to permit the hooking surfaces 56a and 56b to clear each other, the resiliency of the tabs 58b and 58a will urge the hooking surfaces 56a and 56b towards each other to force them to engage, as shown in FIG. 4. Thus, the biasing tabs 64 cooperate with the latch hooks 36 to engage the latch 35 and thereby retain the spring 14 between the plates 10. These tabs 64 also reduce the risk that the latch 35 may be inadvertently disengaged since it is apparent that their resiliency must be overcome before the hooking surfaces 56 can disengage.

When the latch 35 is disengaged, the force of the compressed conical spring 14 will exert a biasing force on the central members 16 to separate the plates 10. Note that the spring force, the biasing or separating force, and the spring axis are all in the direction of expansion of the reservoir, as shown in FIGS. 7 and 9. Since the reservoir 40 is sealed from the atmosphere, such force creates a vacuum which draws fluid from the patient into the reservoir 40. Referring to FIGS. 6 and 7, as the plates 10 separate, the reservoir 40 will form side walls 68,69 (FIG. 6) which conform to the trapezoidal cut-outs 21,22, respectively. The wall 69 is on the opposite side of the reservoir 40 from the wall 68. Since the reservoir 40 is stretched across the cut-outs 21,22, in the direction indicated by the arrow 41, the reservoir walls 68,69 will not be sucked between the plates 10, but rather, will remain more or less perpendicular to the plates 10 as the reservoir 40 fills with fluid. This prevents any sudden changes in reservoir vacuum and permits the reservoir 40 to gradually expand in volume as the plates 10 separate. Thus, the reservoir 40 will have a defined, gradually changing, shape throughout its filling range.

The spring 14 and the unique geometry of the plates 10 cooperate to permit the reservoir 40 to draw a substantially constant vacuum through its entire filling range. "Substantially constant" means that the vacuum level does not fluctuate by more than 20%. Such cooperation may be more fully understood through reference to FIGS. 8, 9, and 10. Referring initially to FIG. 8, it is well known that the force of a compression spring varies inversely to the distance it expands from a fully compressed state. Thus, when a spring is fully compressed, its force is at a maximum, and when it fully relaxes, its force is zero. This relationship is defined by the expression:

$$F = A - KX \tag{1}$$

where F is the force, A is the force at full compression, K is a constant, and X is the distance the spring relaxes from full compression. This expression is represented graphically by a curve 70 of FIG. 8. The constant K is typically referred to as the spring constant, and it defines the slope of the curve 70. It is apparent that, if it were possible to obtain a spring with a spring constant of zero, as indicated by the curve 72, the force exerted by the spring would always be a constant value. Such a spring would make the design of a constant vacuum fluid evacuator a relatively simple matter. For example, it is apparent that a spring with a zero spring constant interposed between two plates connected by bellows could be made to achieve the desired constant vacuum result. Unfortunately, however, a spring having a spring constant of zero would be infinitely long, since the spring, in order to maintain constant force, could never be permitted to fully relax. Thus, as a practical matter, a compromise must be drawn between the spring constant and the length of the spring.

The unique plate geometry of the present invention permits such compromise. Specifically, the plate geometry compensates for the decreasing spring force as the spring 14 expands from a fully compressed state and thereby permits maintenance of a substantially constant pressure within the reservoir 40. It will be recalled that each of the plates 10 is articulated by hinging the wing members 18,20 to their respective central members 16. Comparing FIGS. 2 and 3 with FIGS. 6 and 7, it can be seen that, as the plates 10 are forced apart by the spring 14, the wing members 18,20 pivot inward with respect to the central members 16. This permits the effective plate area over which the spring force is applied to concomitantly decrease. Thus, the effective plate area decreases as the spring force decreases, and therefore, the force per unit of effective area remains more nearly constant. Since the vacuum within the reservoir 40 is proportional to the force per unit area applied to the plates 10, the vacuum will also be more nearly constant.

Figure 13:
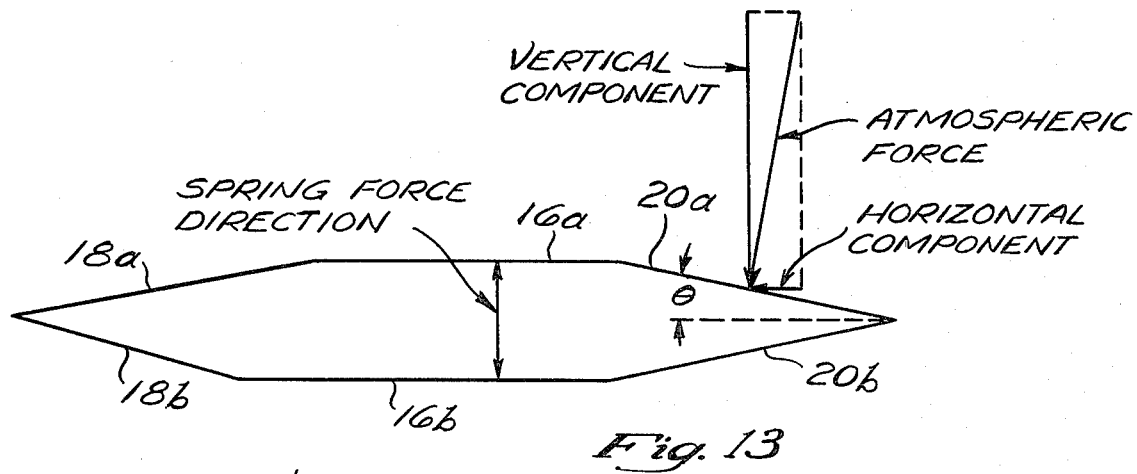
FIG. 13 is a schematic drawing of the reservoir, partially expanded, showing the atmospheric forces on the wing members resolved into two components, namely a vertical component, parallel to the direction of spring force, and a horizontal component, perpendicular to the direction of spring force.
Figure 15:
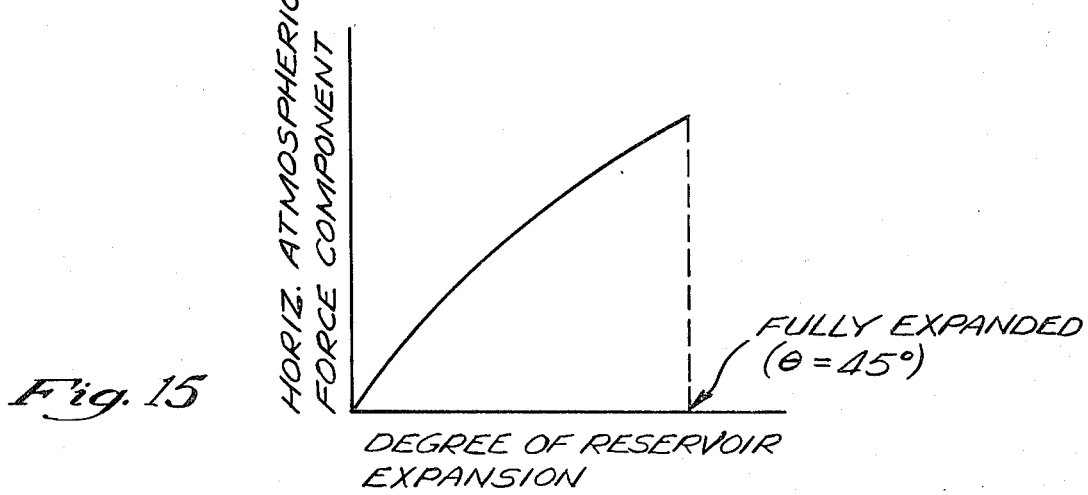
FIG. 15 is a graph showing the magnitude of the horizontal atmospheric force component, shown in FIGS. 13 and 14, as a function of reservoir expansion.

The geometry of the plates 10 also supplements the spring force as the wing members 18,20 pivot inward. This may be understood more fully by comparing the position of the wing members 18,20 with respect to the central members 16, shown in FIG. 3, with that shown in FIG. 7. Referring initially to FIG. 3, when the spring 14 is fully compressed, the wing members 18,20 lie in the same horizontal plane as the central members 15. Thus, the forces generated by the spring 14 between the plates 10 and the opposing forces created by atmospheric pressure will both be directed vertically. However, as the wing plates 18,20 pivot inward, as shown in FIG. 7, it is apparent that the direction of the opposing atmospheric forces applied to the wing members 18,20 will incline from the vertical toward the horizontal, as shown on FIGS. 13 and 14. Thus, comparing FIGS. 13 and 14, the forces on the wing members 18,20 will have a decreasing vertical component and an increasing horizontal component, as they pivot inward at progressively increasing angles with respect to the central members 16. Such horizontal component will increase in magnitude as the reservoir expands, as shown in FIG. 15, to drive the wing members 18,20 inward. Since the wing members 18,20 are connected to their respective central members 16 by the hinges 17, the inward movement of the wing members 18,20 will result in a force which will wedge the central members apart. Thus, the spring force is supplemented by such horizontal forces on the wing members 18,20.

The reservoir 40 also interacts with the wing members 18,20 to supplement the horizontal component force, described above, to drive the wing members 18,20 inward and the central members apart. It will be recalled that the reservoir is stretched between the ends of the wing members 18,20, and across the trapezoidal cut-outs 21,22 to permit the reservoir side walls 68,69 (FIG. 6) to remain more or less perpendicular to the central members 16 as the plates 10 spread apart. Thus, atmospheric pressure will exert force against such perpendicular reservoir walls 68,69. This will pull the ends of the wing members 18,20 toward each other and thereby provide a supplementary force which assists in driving the wing members 18,20 inward. In addition, since the reservoir 40, as previously mentioned, is stretched between the ends of the wing members 18,20, such stretching will provide a further supplementary force to pivot the wing members 18,20 inward relative to the central members 16.

Therefore, the unique geometry of the plates 10 provides compensation for the decrease in spring force as the plates 10 spread apart, and thereby permits the negative pressure within the reservoir 40 to remain substantially constant (i.e., within 20%) throughout the entire filling range.

Referring to FIG. 9, and disregarding any forces created by the interaction of the plates 10 with the reservoir 40, the forces acting on the geometry of the plates 10 may be defined as follows:

$F_S$ = the spring force required to maintain a constant vacuum in the reservoir 40;

R = the horizontal component of the atmospheric forces acting on the wing members 18,20 of the reservoir 40;

U = the vertical force on the central members 16 caused by the force R due to the interaction of the wing members 18,20 with the central members 16; and $V_r$ = the vacuum in the reservoir 40.

In addition, the plate geometry may be defined by the terms listed below:

$\theta$ = one half of the angle formed by the wing member 18a with the wing member 18b or the wing member 20a with the wing member 20b;

$A_C$ = the area of one of the central members 16; and $A_W$ = the area of one of the wing members 18,20.

Since pressure or vacuum equals force divided by area, $V_R$ may be expressed as follows:

$$V_R = [F_S/(A_C + 2A_W \cos\theta)] + 2U \qquad (2)$$

where $A_C + 2A_W \cosine \theta$ is the effective plate area (i.e., the projection of the area of each plate in the direction of spring force) acted upon by the spring; and likewise, $V_R(A_C + 2A_W \cos\theta)$ equals the effective atmospheric force opposing the biasing force. Solving equation (2) for $F_S$ yields:

$$F_S = V_R[A_C + 2A_W \cos\theta] = 2U \qquad (3)$$

The force R may be expressed as a function of the vacuum, $V_R$ as follows:

$$R = 2V_R A_W \sin\theta \qquad (4)$$

And, the relationship between R and U is:

$$2U = R \tan\theta \qquad (5)$$

Substituting (4) and (5) into (3), it may be found that:

$$F_S = V_R[A_C + A_W(\cos\theta - \sin\theta \tan\theta)] \qquad (6)$$

Since $V_R$, $A_C$, and $A_W$ are all constants for a given plate geometry, this expression defines spring force as a function of the angle theta. However, it should be emphasized that this expression is only an approximation of spring force, since it does not take into account the ineraction of the reservoir 40 with the plates 10. Therefore, minor refinement of the plate geometry by emprical means may be necessary.

The distance between the central members 16 may be defined by the expression:

$$X_R = 2H_W \sin\theta \qquad (7)$$

where $X_R$ is the distance between the central members 16, $H_W$ is the trapezoidal height of one of the wing members 18,20, and theta is one-half of the angle formed by the wing member 18a with the wing member 18b or the wing member 20a with the wing member 20b. Thus, since $H_W$ is a constant, this expression defines distance between the central members 16 as a function of theta.

Therefore, by solving the two equations (6) and (7) for various values of the angle theta, a graph of the spring force necessary to achieve a constant vacuum versus the distance between the central members 16 may be developed. Such a graph for a desired vacuum of 1 psi, central member 16 dimensions of 3½ inches by 3¾ inches, and wing members 18,20 dimensions of 3¾ by 5¾ by 1⅜ inches is illustrated by the curve 74 of FIG. 10. While the curve 74 is not exactly linear, it approaches linearity through $\theta = 45$ degrees. Further, it is believed that the previously described interaction of the reservoir 40 with the plates 10 increases the linearity of the curve 74 through this operating range of the reservoir 40. Test results also support the conclusion that the curve 74 is, in reality, more linear than the mathematical approximation illustrated by FIG. 10. Thus, a spring having a linear force versus distance relationship will approximate the force versus distance characteristics of the curve 74. Further, the slope of the curve 74 is sufficiently steep to permit such spring to be of a reasonable length. It should be noted, however, that the curve 74 may be approximated by a linear curve only from zero degrees to 45 degrees of the angle theta. Beyond 45 degrees, the deviation between the curve 74 and a linear curve rapidly increases. Thus, if the distance between the central plates 16 increases significantly beyond a theta of 45 degrees, such deviation will cause the negative pressure within the reservoir 40 to vary substantially from its desired constant value. To avoid this, the trapezoidal cut-outs 21,22 formed by the central members 16 and wing members 18 and 20 of the respective plates 10 are sized to limit the maximum volume of the reservoir 40 to a value which limits the maximum distance between the central members 16 to the equivalent of 45 degrees of the angle theta. This requires that the depth of the cut-outs 21,22, represented by the dimension 80 (FIG. 2) be one-half of the maximum distance between the central members 16. Such maximum distance, which is also equal to the maximum height of the side walls 68,69 (FIG. 6), may be calculated by using equation (7), discussed in reference to FIG. 9, and substituting 45 degrees for theta. Thus, given that: $X_R = 2H_W \sin\theta$, and $\theta = 45$ degrees, then: $X_R = 2H_W(0.707)$ or: $X_R = 1.414 H_W$.

Since the dimension 80 of the cut-outs 21,22 is one-half of the distance between the members 16 when theta is 45 degrees,, or one-half of 1.414$H_W$, such dimension, therefore, is equal to 0.707 $H_W$, where $H_W$ (FIG. 9) is the trapezoidal height of one of the wing members 18,20. Thus, by sizing the depth of the cut-outs 21,22 to equal 0.707 $H_W$, the maximum distance between the plates 16 is limited to the equivalent of 45 degrees of the angle theta.

As previously mentioned, the curve 74 of FIG. 10 may be approximated by a spring having a linear force versus distance relationship. However, it will be recalled that such approximation is valid only from zero degrees to 45 degrees of theta. Thus, to take full advantage of the unique plate geometry, the spring should preferably be under full compression when theta equals zero degrees. Since the plates 10 lie flat against one another when theta equals zero degrees, the spring, therefore, should be conical to permit it to be compressed flat therebetween. It is well known, however, that the strength of a spring coil is inversely proportional to its diameter. The coils of a conical spring, therefore, typically vary in strength, since their diameters necessarily vary. Thus, upon expansion, the coils become progressively active, rather than simultaneously active, and the force versus distance relationship of the spring is consequently non-linear. Therefore, a typical conical spring is incapable of providing the linear force versus distance relationship necessary to approximate the curve 74.

The conical spring 14 of the present invention, therefore, is adapted to permit its coils to be simultaneously active, and thus, unlike typical conical springs, the spring 14 has a linear force versus distance relationship. This is accomplished by increasing the pitch between the coils as the coil diameter increases. Such increasing pitch offsets the loss of the spring force caused by the increasing coil diameter, and thereby permits each of the coils of the conical spring 14 to be simultaneously active. Therefore, the force versus distance relationship of the spring 14 is substantially linear.

The relationship between the coil diameter and coil length for a single coil spring is defined by the expression:

$$X_L = (8A/GD^4)D^3 \tag{8}$$

where $X_L$ is the relaxed length of the single coil, A is the desired force of the coil when fully compressed, G is the modulus of the wire, d is the wire diameter, and D is the coil diameter. Since A is the desired force of the spring, which is a constant, and G and d depend on the type of spring wire used and are also constants, the expression $8A/Gd^4$ will be a constant, or K'. Thus, for a spring of given material and given force, the coil length is equal to the cube of the coil diameter times the constant K', and equation (8) may be rewritten as:

$$X_L = K'D^3 \tag{9}$$

This expression forms a curve 76, as shown in FIG. 11. Through an iterative process, various points on the curve 76 are chosen to produce a series of coils having progressively decreasing diameters which, when connected, form a spring of the desired conical shape. Such conical shape should, of course, permit the coils to nest within one another when the spring is fully compressed. Further, the largest coil diameter should not exceed either dimension of the central plates 16 to permit it to be retained by the spring cup 34. It should be noted that, since coils of decreaseing diameter must be joined together to form the conical spring, each coil will have a diameter on one end that is smaller than that of the other end. Thus, the coil diameters of the curve 76 represent mean coil diameters, and the end diameters of the coils must be adjusted accordingly to permit the coils to be joined together to form a conically-shaped spring. As will be apparent to those skilled in the art, such adjustment may be accomplished during the winding of the spring with the mean coil diameter and coil pitch serving as guidelines. It has been found that the following mean coil diameters produce an essentially conical spring that permits the coils to nest when fully compressed:

Coil #1—1.5
Coil #2—1.88
Coil #3—2.25
Coil #4—2.5

Preferably, the modulus of the wire is $11 \times 10^6$ psi, the wire diameter is 0.1 inch and the force at full compression is about 25 pounds. The spring wire is uniform in diameter throughout its length. Given these values, the pitch of each of the above-listed coils may be calculated, using equation (8), as follows:

Coil #1—0.6
Coil #2—1.19
Coil #3—2.05
Coil #4—2.8

It should, however, be emphasized that, whatever spring characteristics are chosen, the maximum stress on the spring, when fully compressed, should be no more than about one-half of its yield point stress. This permits the spring to be stored for substantial periods of time in its fully compressed state without seriously affecting the spring characteristics.

The conical spring 14 is formed according to the foregoing inventive concepts to generate a substantially linear force versus distance curve which approximates the desired force versus distance curve 74 (FIG. 10) created by the plate geometry. Thus, since the curve 74 defines the spring characteristics necessary to maintain a constant vacuum within the reservoir 40, and the spring 14 approximates such spring characteristics, the reservoir vacuum will be substantially constant throughout its filling range. Test results using the plate geometry and spring coil diameters previously described confirm that a substantially constant vacuum (i.e., within 20%) may be achieved through 45 degrees of theta, as shown by the curve 78 of FIG. 12.

Although the above-described plate geometry is designed to interact with a spring having a linear force versus distance relationship, it will be understood that the plate geometry may be changed to permit it to interact with springs having various other force/distance relationships, so long as the plate geometry reduces the effective plate area against which the spring force is applied at a rate which permits concomitant reductions in spring force to produce a substantially constant vacuum in the reservoir. In other words, a substantially constant vacuum may be achieved by using various combinations of plate geometry and springs, provided that the force versus distance requirements defined by the plate geometry at least approximate the force versus distance characteristics of the spring.

Referring to FIG. 12, approximately 350 cc of fluid will have been drawn into the reservoir 40 when theta reaches 45 degrees. Since the dimensions of the reservoir 40 prevent the plates 10 from separating beyond a distance equivalent to a theta of 45 degrees, the reservoir vacuum will not be maintained thereafter, and therefore, the vacuum will rapidly decrease to zero. An additional amount of fluid will be drawn into the reservoir during the period that such decrease of the reservoir vacuum occurs. Such additional fluid will be accommodated by the reservoir 40, since, as the vacuum decreases, the side walls 68,69 will be permitted to bow outward.

The reservoir 40 should preferably be of a polyvinyl chloride material having a thickness of 0.010 inch to 0.030 inch and a durometer shore A of 75 to 100. Such reservoir material has sufficient flexibility to permit the plates 10 to separate without being inhibited by the reservoir 40. However, the material is sufficiently inelastic to permit it to maintain its shape and prevent deformation due to the weight of fluid in the reservoir 40. Further, the material is sufficiently strong to resist puncturing, and is compatible with gamma-radiation sterilization.

The plates 10 are preferably formed of a polypropylene material, which is also compatible with gamma-radiation sterilization. Such material is sufficiently rigid to prevent the spring 14 from deforming the plates 10 and is sufficiently strong to permit the hooking surfaces 56 of the latch 35 to hold the plate 10 together. However, the material is sufficiently flexible and resilient to permit the biasing tabs 64 and the integrally formed or "living" hinges 17 of the plates 10 to function properly.

What is claimed is:

1. A surgical evacuation device for drawing fluid from a wound, comprising:
   a compressible reservoir, having a pair of structural walls, and a flexible wall member, extending from said structural walls, to seal said reservoir from the atmosphere, the geometrical configuration of said reservoir controlled by said structural walls, as said reservoir expands;

a fluid collection tube connected to said reservoir for draining fluid from said wound to said reservoir; and spring means for providing a biasing force in the direction of expansion of said reservoir, said force biasing said structural walls apart to expand said reservoir and create a vacuum therein, said force decreasing as said reservoir expands, said geometrical configuration producing a wall area projected in the direction of said biasing force, and acted upon by said biasing force, which area decreases as said reservoir expands to at least partially offset the decreasing biasing force provided by said spring to reduce changes in reservoir vacuum and maintain vacuum level.

2. A surgical evacuation device, as defined in claim 1, wherein each of said structural walls comprises a central member and a pair of wing members hinged to said central member on opposite sides thereof, said wing members pivoting with respect to said central member as said walls are biased apart by said spring means to provide said decrease in said area.

3. A fluid evacuation device, as defined in claim 2, wherein said wing members react with atmospheric pressure on the surface of said wing members to force said wing members to pivot relative to said central members and to wedge against said central members to force said central members apart, said wedging supplementing said spring force to further reduce changes in reservoir vacuum.

4. A fluid evacuation device, as defined in claim 1, wherein said vacuum deviates less than 20% from a nominal value throughout the entire operating range of said evacuation device.

5. A fluid evacuation device, comprising:
a compressible reservoir, comprising:
a pair of structural articulated walls, each of said walls comprising a central wall member and a pair of wing wall members, said wing wall members hinged to said central wall member on opposite sides thereof, said central wall member and said respective wing wall members shaped to form trapezoidal cut-outs on opposite sides of each of said articulated walls;
a flexible membrane spanning over and across each of said cut-outs to seal the area between said walls from the atmosphere;
spring means interposed between said walls for biasing said walls apart to expand said reservoir and create a vacuum therein, said spring decreasing in force as said reservoir expands and oriented with the spring axis in the direction of expansion of said reservoir, said wing members pivoting with respect to said central member as said articulated walls are biased apart by said spring means to decrease the component of atmospheric forces acting on said wing members in the direction of the force of said spring means, to at least partially offset the decreasing force of said spring means to reduce changes in reservoir vacuum; and
a fluid collection tube, connected to said reservoir, for conducting fluid from a wound to said reservoir.

6. A fluid evacuation device, as defined in claim 5, wherein said wing members are trapezoidal in shape and said trapezoidal cut-outs are sized to have a trapezoidal height of approximately 0.7 times the trapezoidal height of either of said wing members.

7. A surgical fluid evacuator, comprising:
a reservoir, comprising:
a first articulated wall;
a second articulated wall; and
means for sealing an area between said first and second articulated walls to form a reservoir between said walls while permitting said articulated walls to spread apart;
means for biasing said articulated walls apart to create a vacuum for drawing fluid into said reservoir;
a latch, internal to said reservoir, for holding said walls together with virtually no space therebetween, said latch releasable to permit said first and second articulated walls to spread apart; and
a fluid collection tube, connection to said reservoir, for drawing fluid from a wound to said reservoir.

8. A fluid evacuation device, as defined in claim 7, wherein the thickness of said reservoir, when said articulated walls are held together by said latch, is less than one-half inch.

9. A fluid evacuation device, as defined in claim 7, wherein said flexible wall means conforms to the shape of said articulated wall means as said reservoir expands.

10. A fluid evacuation device, as defined in claim 7, wherein said latch means is integral with said articulated wall means.

11. A fluid evacuation device, comprising:
a reservoir, comprising:
a first articulated wall;
a second articulated wall; and
flexible wall means for sealing an area between said first and second articulated walls to form a reservoir between said walls while permitting said articulated walls to spread apart;
means for biasing said articulated walls apart to create a vacuum for drawing fluid into said reservoir; and
a latch, internal to said reservoir, adapted to selectively hold said articulated walls together with virtually no space therebetween, said reservoir pre-evacuated with respect to the atmosphere to assist said latch in holding said articulated walls together and to prevent deformation of said latch when said surgical evacuator is stored.

12. A fluid evacuation device, comprising:
a reservoir, comprising:
a first articulated wall;
a second articulated wall; and
flexible wall means for sealing the area between said first and second articulated walls to form the reservoir between said walls while permitting said articulated walls to spread apart;
means for biasing said articulated walls apart to create a vacuum for drawing fluid into said reservoir;
a fluid collection tube, connected to said reservoir, for conducting fluid from a wound to said reservoir; and
a latch, internal to said reservoir, adapted to selectively hold said articulated walls together with virtually no space therebetween, said latch comprising:
a first latch hook on said first articulated wall;
a second latch hook on said second articulated wall;
a first biasing tab on said first articulated wall;

a second biasing tab on said second articulated wall; and said first hook cooperating with said second biasing tab and said second hook cooperating with said first biasing tab to engage said hooks when said first articulated wall is pressed against said second articulated wall.

13. A fluid evacuation device, as defined in claim 12, wherein said first and second latch hooks include first and second biasing cam surfaces, first and second closing cam surfaces, and first and second hooking surfaces, respectively, said first and second closing cam surfaces cooperating to move said hooking surfaces to a position which permits them to be engaged and to simultaneously bias said first and second biasing cam surfaces against said second and first biasing tabs, respectively, to bend said tabs in opposite directions, said tabs having sufficient resiliency to engage said hooking surfaces by urging them towards each other when said closing cam surfaces have moved said hooking surfaces to said position which permits them to engage.

14. A fluid evacuation device, as defined in claim 13, wherein said first and second hooking surfaces are parallel to each other and are inclined relative to said articulated walls.

15. A fluid evacuation device, comprising:
a reservoir, comprising:
first articulated wall means comprising a first wing wall member pivotally connected to a first central wing member by a first hinge;
second articulated wall means comprising a second wing wall member pivotally connected to a second central wall member by a second hinge, said first and second wing wall members fastened together to prevent them from sliding relative to each other, said first and second hinges positioned to permit said wing wall members to pivot relative to said central wall members and formed to force said first and second central wall members to slide relative to each other when said first and second wing wall members pivot relative to said central wall members; and
flexible wall means for sealing the area between said first and second articulated wall means to form said reservoir between said wall means while permitting said articulated wall means to spread apart;
means for biasing said articulated wall means apart to create a vacuum for drawing fluid into said reservoir, said articulated wall means formed to permit them to lie flat against each other when said biasing means is compressed;
a fluid collection tube, connected to said reservoir for conducting fluid from a wound to said reservoir; and
latch means internal to said reservoir, for selectively holding said first and second articulated wall means together with virtually no space therebetween, said latch means disengaged by said relative sliding of said central wall members.

16. A fluid evacuation device, as defined in claim 15, wherein:
the pivot points of said first and second hinges are at the exterior surfaces of said first and second articulated wall members, respectively;
said articulated wall members have respective internal surface slots aligned with said hinge pivot points, one of said slots narrowing and the other of said slots widening when said wing wall members pivot about said hinges relative to said central wall members; and
said slots are sized to permit said narrowing and widening of said slots to slide said central wall members relative to each other through a distance sufficient to disengage said latch.

17. A surgical evacuation device, comprising:
a compressible skeletal articulative mechanism;
a flexible membrane conforming in shape to said skeletal mechanism for sealing said skeletal mechanism to the atmosphere to form a reservoir, said skeletal mechanism providing a structure for controlling the shape of said reservoir;
a fluid collection catheter sealed to said membrane; and
means for biasing said skeletal mechanism to expand said reservoir to draw fluid through said catheter into said reservoir, said biasing means providing a biasing force in the direction of expansion of said reservoir, said force decreasing as said skeletal mechanism expands, the expansion of said skeletal mechanism changing the shape of said reservoir to reduce the component of atmospheric forces directed parallel to said biasing force to at least partially offset for decreases in said biasing forces.

18. A surgical evacuation device, as defined in claim 17, additionally comprising:
a latch, connected to said skeletal mechanism, and internal to said reservoir, for retaining said skeletal mechanism in a compressed state, said latch releasable to permit said biasing means to expand said reservoir.

19. A surgical evacuation device, as defined in claim 18, wherein said reservoir is pre-evacuated with respect to the atmosphere to assist said latch in retaining said skeletal mechanism in a compressed state.

20. A surgical evacuation device, as defined in claim 17, wherein the thickness of said skeletal mechanism, when compressed, is less than one-half inch.

21. A surgical evacuation device, as defined in claim 17, wherein said skeletal mechanism comprises a pair of plates and wherein said biasing means comprises a spring interposed between said pair of plates, said spring including coils which nest within one another to permit said plates to lie flat against one another when said spring is fully compressed.

22. A surgical evacuation device, as defined in claim 17, additionally comprising:
a drain tube extending through and sealed to said membrane, said drain tube having perforations throughout its extension into said reservoir to permit said reservoir to be drained when the end of said drain tube is blocked.

23. A fluid evacuator for drawing fluid from a wound, comprising:
a pair of structural articulated plates;
an expandable reservoir for containing fluid, said reservoir providing means for sealing the area between said plates from the atmosphere, and conforming to the configuration of said plates as said reservoir fills;
a spring, interposed between said plates and compressed to provide biasing force, in the direction of expansion of said reservoir, to bias said plates apart to expand said reservoir and create a vacuum therein, said spring force in the same direction as said biasing force and decreasing as said reservoir expands;

said plates interacting with said spring and said reservoir to cause the component of atmospheric forces on said reservoir in a direction parallel to said spring biasing force to decrease as said reservoir expands, and to cause the component of atmospheric forces acting on said reservoir in a direction perpendicular to said spring biasing force to increase as said reservoir expands, to provide a supplementary force to assist said spring in biasing said plates apart, said supplementary force increasing as said reservoir expands, said decreasing atmospheric force and said increasing supplementary force cooperating with the force of said spring to reduce changes in said vacuum as said reservoir expands; and a fluid collection tube, for conducting fluid into said reservoir.

24. A surgical fluid evacuator, comprising:

a reservoir, comprising:

a pair of structural articulated plates;

flexible wall means for sealing the area between said plates from th atmosphere to form a reservoir between said walls while permitting said plates to spread apart;

a fluid collection catheter for conducting fluid into said reservoir; and spring means interposed between said plates, said spring means biasing said plates apart to expand said reservoir and create a vacuum therein, said plates controlling the geometry of said reservoir during expansion to provide at least partial compensation for changes in said vacuum caused by changes in the force of said spring means as said spring means expands, said compensation providing a substantially constant vacuum.

25. A surgical fluid evacuator, comprising:

a reservoir;

a fluid collection catheter for conducting fluid into said reservoir; and a spring, disposed within said reservoir, having coils comprised of wire having a uniform wire diameter, said spring providing a force to bias the walls of said reservoir to create a vacuum therein, said coils formed to permit them to nest within each other when fully compressed, and formed to permit all of said coils, when compressed, to be active.

26. A surgical fluid evacuator, as defined in claim 25, wherein the mean diameters of said coils vary directly, but non-linearly, with their pitch.

27. A method of controlling changes in vacuum in a surgical evacuation reservoir, comprising:

biasing said reservoir to expand, using a spring which provides a biasing force in the direction of expansion of said reservoir;

causing said biasing force to reduce at a first predetermined rate as said reservoir expands;

reducing the effective area of said reservoir, projected in the direction of said biasing force of said spring, at a second predetermined rate as said reservoir expands; and coordinating said first and second predetermined rates to limit changes in said vacuum in said reservoir.

28. A method of limiting changes in vacuum in a surgical evacuation reservoir, as defined in claim 27, wherein said first predetermined rate and said second predetermined rate are approximately equal to permit said vacuum to be substantially constant.

* * * * *